(12) United States Patent
Jarvis et al.

(10) Patent No.: US 7,851,434 B2
(45) Date of Patent: Dec. 14, 2010

(54) AMYLOID AND AMYLOID-LIKE STRUCTURES

(75) Inventors: Suzanne P. Jarvis, Dublin (IE); Anika S. Mostaert, Dublin (IE)

(73) Assignee: The Provost, Fellows and Scholars of the College of the Holy and Undivided Trinity of Queen Elizabeth Near Dublin, Dublin (IE)

( * ) Notice: Subject to any disclaimer, the term of this patent is extended or adjusted under 35 U.S.C. 154(b) by 368 days.

(21) Appl. No.: 11/685,443

(22) Filed: Mar. 13, 2007

(65) Prior Publication Data

US 2007/0266892 A1 Nov. 22, 2007

(30) Foreign Application Priority Data

Mar. 15, 2006 (IE) .............................. S2006/0202

(51) Int. Cl.
    *C07K 14/00* (2006.01)
(52) U.S. Cl. .............................. 514/2; 530/300; 530/350
(58) Field of Classification Search ....................... None
    See application file for complete search history.

(56) References Cited

U.S. PATENT DOCUMENTS

| 5,383,999 A | 1/1995 | Kuo |
| 6,176,917 B1 | 1/2001 | Duclaud et al. |
| 6,376,636 B1 | 4/2002 | Hansma et al. |

FOREIGN PATENT DOCUMENTS

| GB | 728 537 A | 5/1955 |
| WO | 00/17328 | 3/2000 |
| WO | 02/42321 | 5/2002 |
| WO | 02/081104 A | 10/2002 |
| WO | 2004/007532 A2 | 1/2004 |
| WO | 2005/033131 | 4/2005 |

OTHER PUBLICATIONS

Deruere et al., "Fibril assembly and carotenoid overaccumulation in chromoplasts: a model for supramolecular lipoprotein structures", The Plant Cell 6(1): 119-133 (1994).*
West et al., "De novo amyloid proteins from designed combinatorial libraries", Proc. Natl. Acad. Sci. USA 96: 11211-11216, Sep. 1999.*
Bouma et al., "Glycation induces formation of amyloid cross-beta structure in Albumin", The Journal of Biological Chemistry, 278(43): 41810-41819 (Oct. 2003).*
Product Information Sheet for Albumin from Bovine Serum, Sigma-Aldrich (downloaded May 10, 2010).*
Westermark, P. et al. Amyloid Fibril Protein Nnomenclature—2002; Amyloid: J. Protein Folding Disord.; Sep. 1, 2002; pp. 197-200.
Fletcher, R. L. et al.; The Settlement, Attachment and Establishment of Marine Algal Spores; British Phycological Journal, vol. 27; Sep. 1, 1992; 303-329.
Loske, C. et al.; Transition Metal-mediated Glycoxidation Accelerates Cross-linking of (β-amyloid Peptide; Eur. Journal Biochem, vol. 267, May 9, 2000; pp. 4171-4178.

Sever, M. J., et al.; Metal-mediated Cross-linking in the Next Generation of a Marine-mussel Adhesive; Angewandte Chemie Int. Ed., vol. 43, 2004; pp. 448-450.
Best, R. B. & Clark, J.; What can atomic force microscopy tell us about protein folding?; Chem. Commun. vol. 18; 2002; pp. 183-192.
Lee, G. U., Chrisey, L. A. and Colton, R. J.; Direct measurement of the interaction forces between complementary strands of DNA with atomic force microscopy; Science, vol. 266; Nov. 4, 1994; pp. 771-773.
Rief, M., Clausen-Schaumann H., and Gaub H.E.; Sequence-dependent mechanics of single DNA molecules; Nature Structural Biology; vol. 6, No. 4; Apr. 1999; pp. 346-349.
Rief, M., Oesterhelt, F., Heymann, B. and Gaub, H. E. Single molecule force spectroscopy on polysaccharides by atomic force microscopy; Science, vol. 275; Feb. 28, 1997; pp. 1295-1297.
Fisher, T. E., Marszalek, P. E. and Fernandez, J. M.; Stretching single molecules into novel conformations using the atomic force microscope; Nature Structural Biology; vol. 7, No. 9; Sep. 2000; pp. 719-724.
Rief, M. Gautel, M. Oesterhelt, F., Fernandez, J. M. and Gaub, H. E.; Reversible unfolding of individual titin immunoglobulin domains by AFM; Science vol. 276; May 16, 1997; pp. 1109-1112.
Tskhovrebova, L., Trinick, J., Sleep, J. A. and Simmons, R. M.; Elasticity and unfolding of single molecules of the giant muscle protein titin; Nature, vol. 387; May 15, 1997; pp. 308-312.
Smith, B. L. et al.; Molecular mechanistic origin of the toughness of natural adhesives, fibres and composites; Nature, vol. 399; Jun. 24, 1999; pp. 761-763.
Fernandez, J. M.; Fingerprinting Single Molecules In Vivo; Biophysical Journal, vol. 89; Dec. 2005; pp. 3676-3677.
Bustamante, C., Marko, J. F., Siggia, E. D. and Smith, S.; Entropic elasticity of n-phage DNA; Science, vol. 265; Sep. 9, 1994; pp. 1599-1600.
Dugdale, T. M., Dagastine, R., Chiovitti, A., Mulvaney, P. and Wetherbee, R.; Single adhesive nanofibers from a live diatom have the signature fingerprint of modular proteins; Biophysical Journal, vol. 89; Dec. 2005; pp. 4252-4260.
Oberhauser, A. F., Marszalek, P. E., Erickson, H. P. & Fernandez, J. M.; The molecular elasticity of the extracellular matrix protein tenascin; Nature, vol. 393; May 14, 1998; pp. 181-185.
Wagner, V. T., Brian, L. and Quatrano, R. S.; Role of vitronectin-like molecule in embryo adhesion of the brown alga *Fucus*; Proc. Natl Acad. Sci. USA, vol. 89; Apr. 1992; pp. 3644-3648.
Levi, B.; Friedlander, M.; Identification of two putative adhesive polypeptides in *Caulerpa prolifera* rhizoids using an adhesion model system; Journal of Applied Phycology, vol. 16; 2004; pp. 1-9.

(Continued)

*Primary Examiner*—Anand U Desai
(74) *Attorney, Agent, or Firm*—Summa, Additon & Ashe, P.A.

(57) ABSTRACT

The present invention describes a methods, uses, compositions such as adhesive, sealants and coatings, scaffold material, composite material, all comprising amyloid-like materials such as fibrils, in particular those made from fruit or vegetable proteins. The amyloid-like materials impart good mechanical strength to the materials in which it is employed. Inhibition of amyloid formation is also described.

7 Claims, 6 Drawing Sheets

OTHER PUBLICATIONS

Dobson, C. M.; Protein Folding and Misfolding; Nature, vol. 426; Dec. 18, 2003; pp. 884-890.

Marsalek, P. E., Oberhauser, A. F., Pang, Y-P. & Fernandez, J. M.; Polysaccharide elasticity governed by chair-boat transitions of the glucopyranose ring; Nature, vol. 396, Dec. 17, 1998; pp. 661-664.

Tycko, R.; Progress towards a molecular-level structural understanding of amyloid fibrils; Current Opinion in Structural Biology; 2004; pp. 14:96-103.

Kellermayer, M. S. Z. et al.; Reversible mechanical unzipping of amloid β-fibrils; The Journal of Biological Chemistry, vol. 280, No. 9; Mar. 4, 2005; pp. 8464-8470.

Lee, G. et al.; Nanospring behaviour of ankyrin repeats; Nature, vol. 440, No. 9; Mar. 2006; pp. 246-249.

Fowler, D. M. et al.; Functional Amyloid formation within mammalian tissue; PloS Biology, vol. 4, Issue 1; Jan. 2006; pp. 0100-0107.

Hamwood, T. E., Cribb, B. W., Halliday, J. A., Kearn, G. C. and Whittington, I. D.; Preliminary characterisation and extraction of anterior adhesive secretion in monogenean (platyhelminth) parasites; Folia Parasitologica vol. 49; 2002; pp. 39-49.

Waite, J. H., Lichtenegger, H. C., Stucky, G. D. and Hansma, P.; Exploring Molecular and mechanical gradients in structural bioscaffolds; Biochemistry; Jun. 22, 2004; pp. 7653-7662.

Kamino, K. et al.; Barnacle Cement Proteins; The Journal of Biological Chemistry, vol. 275, No. 35; Sep. 1, 2000; pp. 27360-27365.

Baxa, U., Speransky, V., Stevens, A. C., and Wickner, R. B.; Mechanism of inactivation on prion conversion of the *Saccharomyces cerevisiae* Ure2 protein; Proceedings of the National Academy of Sciences, vol. 99, No. 8; Apr. 16, 2002; pp. 5253-5260.

van Koningsveld, G.A., Gruppen, H., De Jongh, H.H.J., Wijngaards, G., Van Boekel, M.A.J.S., Walstra, P., and Voragen, A.G.J.; The solubility of potato proteins from industrial potato fruit juice as influenced by pH and various additives; J. Sci. Food Agric., vol. 82; Sep. 24, 2001; pp. 134-142.

van Koningsveld, G.A., Gruppen, H., De Jongh, H.H.J., Wijngaards, G., Van Boekel, M.A.J.S., Walstra, P., and Voragen, A.G.J.; Effects of ethanol on structure and solubility of potato proteins and the effects of its presence during the preparation of a protein isolate; Journal of Agricultural and Food Chemistry, vol. 50; 2002; pp. 2947-2956.

Pearce, F.G., Mackintosh, S.H., and Gerrard, J.A.; Formation of Amyloid-like Fibrils by Ovalbumin and Related Proteins Under Conditions Relevant to Food Processing; Journal of Agricultural and Food Chemistry, vol. 55; 2007, pp. 318-322.

International Search Report of foreign counterpart application No. PCT/IE2007/000037 mailed Oct. 17, 2007.

Fantner, G. E. et al., Sacrificial bonds and hidden length: Unraveling molecular mesostructures in tough materials. Biophysical Journal, vol. 90, (2005); pp. 1411-1418.

Bateman, A. et al., The Pfam protein families database; Nucleic Acids Research; 2004, vol. 32, Database issue pp. D138-D141.

Vowles, G. H. & Francis, R. J. in Theory and Practice of Histological Techniques, 5th ed., editors Bancroft, J. D. & Gamble M.; Churchill Livingstone, Harcourt, London, 2002; pp. 303-324.

Gazit, E., Mechanisms of amyloid fibril self-assembly and inhibition: Model short peptides as a key research tool. The FEBS Journal, 272, 2005; pp. 5971-5978.

Whittington, I. D. & Cribb, B. W., Adhesive secretions in the Platyhelminthes. Advances in Parasitology, vol. 48, 2001; pp. 101-224.

LeVine III, H., Quantification of β-sheet amyloid structures with Thioflavin, T, Methods Enzymol., 1999 Academic Press, 309: pp. 274-284.

\* cited by examiner

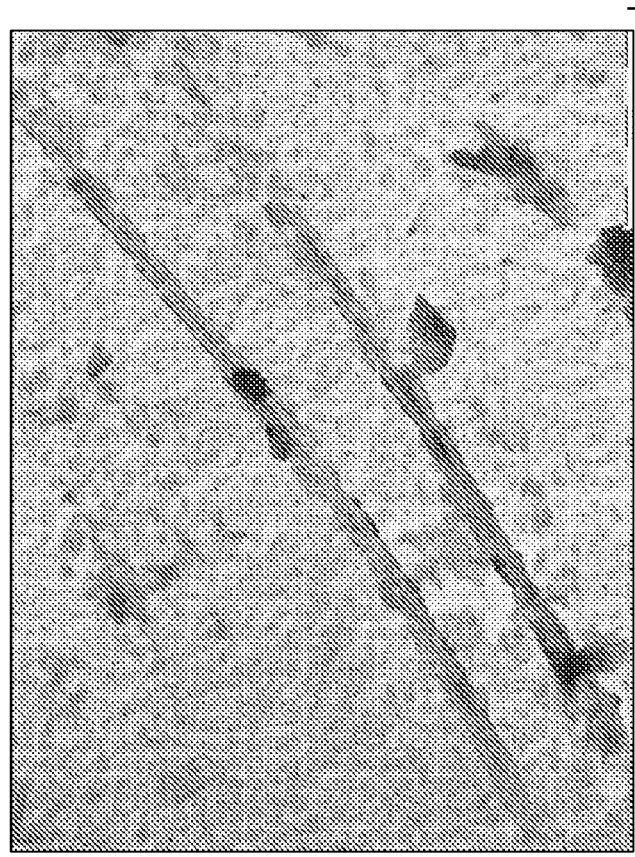
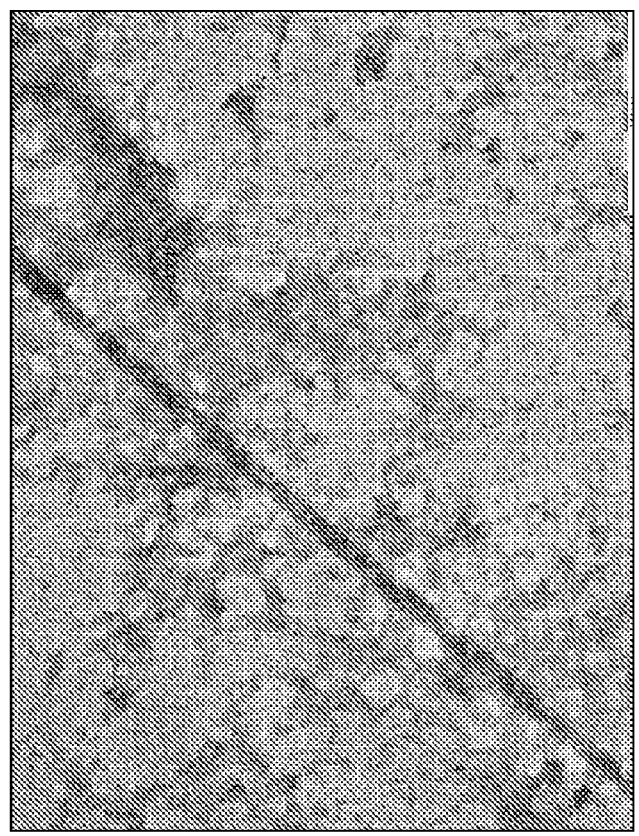
FIG. 7

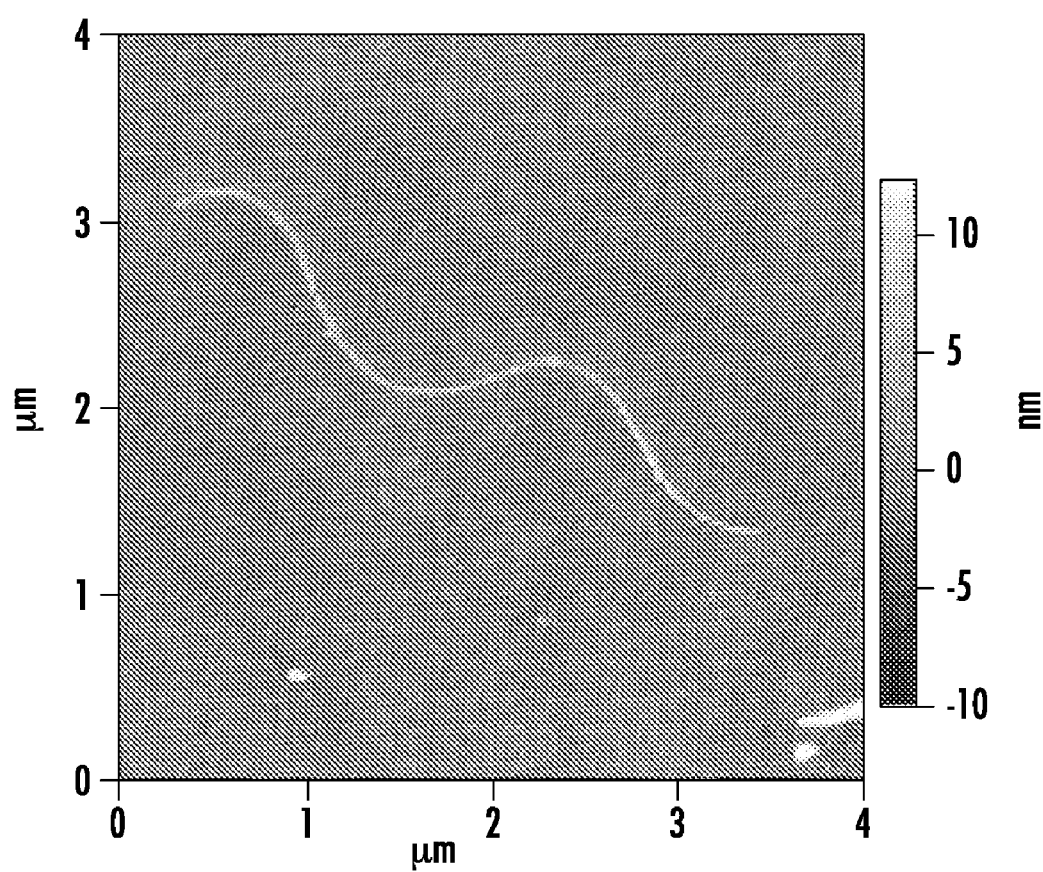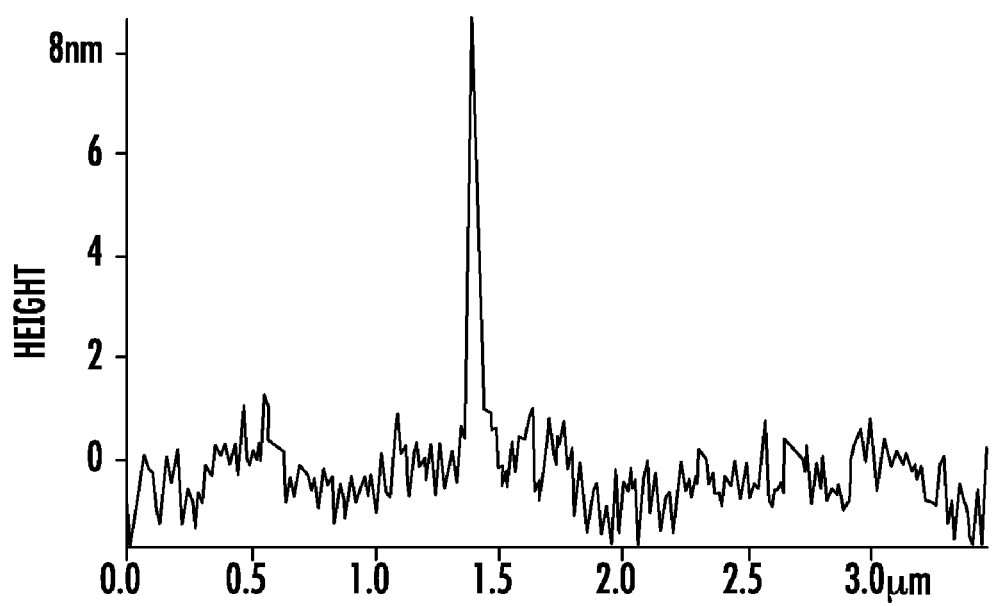
FIG. 8

US 7,851,434 B2

AMYLOID AND AMYLOID-LIKE STRUCTURES

FIELD OF THE INVENTION

The present invention relates to amyloid structures generally and to their properties such as mechanical strength. In particular the present invention relates to amyloid proteins or fibrils formed in vivo and synthetic amyloid-like proteins or fibrils formed in vitro. In one aspect of the invention the mechanical strength of amyloid can be harnessed directly or imparted to other materials including natural and synthetic materials. In another aspect, the present invention relates to amyloids and their role in bonding. A further aspect of the present invention relates to the role of amyloids in inhibition of bonding.

BACKGROUND TO THE INVENTION

Amyloidal structures have been found in the body. Some have been found as plaques and are implicated in the progression of certain diseases. For example the relationship of plaques of amyloidal fibrils to Alzheimer's disease has been extensively studied. Moreover the presence of such plaques has been studied in relation to other diseases such as amyloidisis, diabetes mellitus Type II, Parkinson's disease, Huntington's disease and spongiform encephalopathies such as CJD. Adopting recent recognised nomenclature[1], amyloid is used herein to refer to certain intracellular and extracellular protein aggregations in vivo. In particular within the present invention the term amyloid includes protein with cross beta sheet quaternary structure which is usually in fibrillar form. For amyloid aggregations synthesised from proteins or peptides in vitro we use the term amyloid-like. The structure in question is described in more detail below and with reference to the drawings.

Generally speaking the amyloid or amyloid-like structure can be recognised by many techniques and in particular is known for its strong affinity for the dye Congo red and a typical green-gold birefringence after such staining under cross-polarized light (for samples of optimum thickness). Additionally amyloid or amyloid-like structure can be identified by staining with thioflavin T or thioflavin S. Fibrils can be characterized at the molecular level by x-ray diffraction. In particular, the beta sheet configuration of the amyloid or amyloid-like structure can be recognised by characteristic bands (such as in X-ray diffraction) which correlate to interstrand distances in the beta sheet.

The ability of algae to adhere to a wide range of natural and artificial surfaces in marine, freshwater and terrestrial habitats is thought to be due to the secretion of extracellular polymeric substances (EPS) that have a diversity of structure, chemical composition and function[2]. The mechanism of adhesion typically involve initial, reversible attachment to a surface followed by an EPS secretion that forms a more permanent adhesive[2]. Similar (permanent or temporary) adhesive mechanisms, which involve the deposition of EPS, are found extensively in nature, not only in plants, but also invertebrate organisms such as barnacles and mussels and indeed in other organisms such as parasites and bacteria.

WO 02/042321 (Dobson et al) discloses a method of incorporating peptide into amyloid fibrils. In particular, the document describes a method of creating amyloid fibrils from human plasma protein which have two or more distinct molecular species. The distinct species are said to associate within the beta-sheet array. The document posits creating fibrils which in turn can be used to generate a plastic or scaffold without any supporting examples. The plastics materials are suggested for use as a support to grow cells for grafts or transplant. Controlled disassociation of fibrils is mentioned as being useful for controlled release of drugs. Further mention is made without example of use of gels to encapsulate drugs (capsules are mentioned) or of impregnating a gel with drugs. Fibrils which are tubular with a hollow core or with flat ribbon or twisted morphologies are mentioned as possibilities though again no examples are given. All of the teaching of WO 02/04321 relates to creating materials for use in vivo and formation of the fibrils in vivo with the intention of treating diseases in animals such as those described above.

WO 00/17328 also to Dobson et al, describes amyloid fibrils free of other protein and processes for their preparation. The teaching of WO 00/17328 relates to creating materials for use in vivo and formation of the fibrils in vivo with the intention of treating diseases such as those described above. For example bovine and human amino acid sources are employed. The primary objective of WO 00/17328 is providing treatments for such diseases although mention is made, without example, of having metallised fibrils forming wires for electronics, or fibrils being made into plastics or made into structures.

U.S. Pat. No. 6,376,636 (Hansma et al) describes a modular, energy dissipating material and method for using it. The invention investigates the fracture resistance of the abalone shell. The study included consideration of the energy dissipating properties of Lustrin A. The sawtooth-like pattern was shown to reflect the success of unfolding of folded domains within a single molecule of Lustrin A.

WO 2005/033131 (Larsen et al) discloses production of amyloid fibrils from wheat flour proteins. Wheat proteins and in particular a glutenin material were chosen by Larsen et al because they are rich in glutamine residues (wheat proteins are considered to be relatively large compared to the average protein—possibly 800 residues or more and of those approximately a third are glutamine residues). Glutamine rich material have been thought to be necessary for the formation of amyloid-like structures. Amyloid-like fibrils by Larsen et al were formed from wheat flour over a period of 1 to 3 months.

SUMMARY OF THE INVENTION

The method provides novel and surprising compositions and methods. For example it is possible to render proteins and or peptides into adhesives comprising converting the protein into an amyloid or amyloid-like fibril. For example, in addition to the amyloid materials formed by WO 2005/03313 which include materials formed from protein extracted from wheat, the present inventors have found that amyloid structures, in particular amyloid-like fibrils and ribbons, can be formed from vegetable and fruit proteins for example potato or banana. This is particularly surprising because unlike WO 2005/033131 the proteins from these sources do not have a high glutamine content and are thus not expected to readily form amyloid-like structures. Even more surprisingly, proteins from these sources rapidly form amyloid-like structures which are detectable within days, as opposed to months with the glutenins. In contrast to the assumptions underlying the work of Larsen et al the present inventors believe that having a relatively large number of amino acids (for example greater than 600 amino acids) may make it difficult to denature the materials to and create the Fold structure necessary to from the beta sheet configuration. Reducing the time for forming amyloid-like structures is particularly beneficial as it a much more efficient process and reduces the storage time and energy cost (particularly if the temperature is elevated to speed formation of the amyloid-like structures).

Other suitable sources of protein which may be converted into amyloid-like materials, include beans such as soy, marsh grasses such as rice and plant fibre such as from hemp, or algae. The source desirably does not contain high molecular weight proteins or proteins with a high glutamine content.

The present invention also provides for edible films and/or biodegradable films comprising an amyloid fibril of the invention. Currently, edible films are typically made from wheat gluten, corn zein and milk proteins. By using amyloid-like films produced from vegetable or fruit proteins the present invention provides an edible coating for use in the food and pharmaceutical industry that provides a strong mechanical barrier to moisture, and in addition is suitable for those persons who have a wheat gluten intolerance (e.g. celiac disease) milk protein allergies (e.g. lactose intolerance).

Separation of useable protein from the fruit or vegetable can be done relatively easily utilizing suitable apparatus, for example an apparatus that extracts juice from the vegetable or fruit. On a small-scale an appliance such as a domestic juicer may be utilised. The protein may then be denatured under suitable conditions to form amyloid-like structures. The present inventors have found that amyloid-like fibrils can be formed very quickly even at room temperature.

Generally speaking a transition will take place from soluble protein to insoluble amyloid-like structures once the amyloid-like material is formed.

Method of forming the amyloid-like structures include the following steps:

Extraction of plant juice

Separation of solids from liquid (for example by centrifuging and/or filtering)

Incubation of filtrate at appropriate pH and temperature

In contrast to the dry starting material used by Larsen et al, (Larsen et al employ a flour (dry, solid), separate the proteins and then suspend in solution) the present inventors extract plant juice to obtain proteins which are already in solution.

The present inventors have further found that the formation of amyloid-like material from the protein in question can be pH dependent in some instances. For example, in the case of potato juice, raising the pH value from about 5.9 to about 7.4 ensures good formation of amyloid-like material. Buffering techniques may be employed as necessary to control the pH of the material to optimise formation of amyloid-like material.

If it is desired to form amyloid-like material in situ, then changing the pH of the amyloid precursor environment may be a sufficient control to initiate amyloid formation when desired. Any protein which is a suitable precursor material from which to form amyloid-like material may be employed.

In particular the following buffers are shown to work particularly well for example with formation of amyloid-like structures from potato protein: Phosphate buffered solution (PBS), and Tris HCl.

Pearce et al J. Agric. Food Chem. 2007, 55, 318-322 describes methods for obtaining amyloid fibrils from Ovalbumin and related proteins.

Such methods provide cheap and readily available source of suitable protein for forming amyloid-like structures. The amyloid-like structures produced by such methods may be utilised in any of the envisaged end-use applications of the present invention. For example an adhesive formulation may be formulated by admixing the amyloid-like structure or amyloid precursor (e.g. protein) with a suitable material such as a polysaccharide.

Additionally, catalytic methods may be employed to generate the amyloid structures. (For example auto-catalysis/ seeding, enzymatic catalysis and metal ion catalysis may be employed, which have been independently implicated in the formation of amyloid fibrils in the brain[3] and the function of natural marine based adhesives[4]).

The skilled person will know that other methods of forming amyloid or amyloid-like structures as desired may be employed. For example an activator may be employed to activate amyloid formation from a desired protein. As mentioned, catalytic systems may be employed also to initiate amyloid formation as desired. Any suitable protein denaturant may be employed, for example urea, sodium dodecyl sulphate (SDS) or guanidine hydrochloride.

In particular air-activated, UV activated or heat-activated compositions may be formulated. Anaerobically activated compositions are also possible.

Compositions of the present invention may be formulated as one-part compositions or as two-part compositions. For example, in the case of an activator for activating amyloid or amyloid-like formation, the activator and the protein precursor of material may be held separately for later mixing for use for example upon dispensing. pH activated compositions are also possible. For example, the present invention may be used to provide a composition for use in fluids, particularly liquids and especially water, such that upon contact with the fluid, the pH of the composition alters so as to initiate amyloid-like structure formation and thereby form an adhesive composition. Such compositions are particularly useful in forming compositions in aqueous environments, such as underwater adhesives and adhesives for use in contact with body fluids, for example, on living tissue or cell culture.

Known methods for producing proteins may be employed herein. Such methods which include for example biological sources such as microorganisms which produce the desired protein. In some applications, such microorganisms of the invention can therefore be used to apply adhesive over a period of time in particularly difficult to reach locations, by applying an amount, for example in solution or suitable nutrient broth to the location requiring adhesion, and permitting the microorganisms to excrete the adhesive compositions of the invention.

Cells of the invention (such as those formed on a scaffold structure of the present invention) are also suitable for use in skin grafts and wound healing. Such cells may be particularly suitable for use in tissue regeneration, as the adhesive properties of the cells may promote growth and adherence of the cells on polymeric matrices designed for organ regeneration. The cells may therefore be transformed cells or an altered cell so as to secrete or present on the cell-surface proteins or peptides of the invention. Alternatively, or in combination, the extracellular conditions may be altered (by any of the means as described herein) so as to convert the secreted proteins or cell-surface presented proteins to amyloid-like compositions.

The present invention also comprises an adhesive composition comprising protein in the form of an amyloid fibril or amyloid-like fibril.

Further applications include strengthening applications where the amyloid or amyloid-like structure is utilised to add additional strength to a bond or structure being formed. The amyloid or amyloid-like material can thus be used to add cohesive strength to a bond or structure.

A further aspect of the invention is the ability to reduce bond strength and/or inhibit bonding by employing an inhibitor for amyloid formation. In this respect amyloid formation can be prevented if beta-sheet formation is inhibited. Additional strength with amyloid and amyloid-like materials may be imparted where cross-linking within the material takes place. It may therefore be desirable to inhibit cross-linking where appropriate. Conversely, in certain applications, for example for adhesive purposes it may be desirable to select materials where the cross-linking takes place. For example the polymerisation process to form the beta-sheet is inhibited by including one or more amino acids which are not conducive to beta-sheet formation. One example of such an amino acid is proline. Other active inhibitors may be selected from a group of aromatic residues such as phenylalanine, phenylsulfonphthalein (phenol red), catechins and curcumin, heat shock proteins and combinations thereof. Antifouling compositions are thus within the present invention. Theses include compositions suitable for preventing fouling from water-inhabiting life forms (e.g. seawater). All substrates which temporarily or permanently contact water may thus be protected. As above the present invention may also prevent fouling from bacteria. A further aspect is relates to prevention of fouling by fungi.

The present invention concerns a synthetic adhesive composition comprising an amyloid-like component, the amyloid-like component comprising at least one peptide or protein having an adhesion group.

A further embodiment concerns a synthetic adhesive composition comprising; a curable component and an amyloid-like component. The amyloid-like component will impart mechanical strength to the cure product of the curable component; and if required the adhesive will also comprise a cure component for curing the curable component.

In either of the above mentioned compositions the amyloid-like component may be formed from an amyloid precursor peptide or protein.

Any composition as mentioned above may use the amyloid-like component in-situ for adhesion.

The peptide or protein used in any of the mentioned compositions may be derived from a plant, as described previously or animal source. In particular the peptide or protein used in any aspect of the present invention may be derived from a fruit or vegetable. For example wherein the peptide or protein is a banana or potato peptide or protein. These proteins are large enough to provide sufficient mechanical advantage in the amyloid fold without being so large that a prohibitively long period of time is required to form amyloid fibrils. By using fruit or vegetable derived proteins the risk of allergens and toxins can be reduced.

The amyloid-like material in any of the compositions previously mentioned, may be in the form of fibrils and it may comprise at least one protein. The amyloid-like component may be synthetic.

This invention also concerns a composite material comprising; a fibrous or particulate material which is not formed from an amyloid-like component; a filler material; and an amyloid-like component wherein the synthetic amyloid-like component acts as binder to bind the other components together. The fibrous or particulate material that is contained in such a composite material may contain fibres or particles which have a diameter of at least 0.1 mm.

A composite material as previously mentioned is also suitable for use as a structural building element such as part of a building or piece of furniture. For example it may be used as a binder or a cementious or filler material. In such cases the structural material will be any inorganic particulate material, particularly those derived from a geological source such as rock, sand, gravel, cement etc.

The composite material as mentioned above has further application in that it is suitable for use in medical applications, such as in a dressing, for example bandages, a tissue transplant or graft. A portion of composition can at least form the fibrous material and can act as a tissue scaffold. The portion of amyloid-like material within the compound may be solely responsible for forming such a tissue scaffold.

The composite material mentioned is also suitable for use as a coating or sealant. For example, the composite material may be suitable for coating products for ingestion, such as food or medicinal products.

The composite material may be moisture resistant and also may be employed as a thin film. A further advantage is that the composite material mentioned is resiliently deformable and may also be flexible. Such a composite material has further application for use as a packaging material for example as an alternative to cling film. The composite material, as already mentioned, may contain a filler material. This filler material may be selected from the group consisting of polysaccharides, glycerin, gelatine, agar, agarose and combinations thereof.

The amyloid-like component may form up to 20% w/w of the composite material previously mentioned. Desirably the amyloid-like component forms up to 15% w/w of the composite material, for example, the amyloid-like component forms up to 12% w/w of the composite material.

The invention further includes a scaffold material comprising a fibrous material constructed from an amyloid-like component wherein the amyloid-like component is formed from a suitable precursor material such as a plant protein, for example vegetable such as potato, fruit such as banana, beans such as soy, marsh grasses such as rice and plant fibre such as from hemp, or algae.

Then invention discloses a sealant composition comprising; an amyloid-like component, the amyloid-like component comprising at least one peptide or protein. Another sealant composition is disclosed comprising; a curable component; an amyloid-like component, the amyloid-like component for imparting mechanical strength to the cure product of the curable component; and if required, a cure component for curing the curable component.

Any of the mentioned compositions have further application in the inhibition of amyloid-like material formation, having, as active ingredient, an inhibitor component for inhibiting the formation of amyloid-like material from an amyloidogenic peptide or protein. The active ingredient may be selected from a group of aromatic residues such as phenylalanine, phenylsulfonphthalein (phenol red), catechins and curcumin, heat shock proteins and combinations thereof.

The invention also relates to a method of inhibiting adherence of life forms to a formation surface or structure surface comprising treating the structure surface with an inhibiting agent for inhibiting the formation of amyloid. This inhibiting agent for amyloid formation may be applied to a structure surface. This inhibiting agent may further be applied to a structure that is natural (such as rock) or man-made, for example a building or vehicle such as a ship. Indeed the methods of the present invention can be employed to prevent any undesired bio-fouling, for example by micro-organisms. Applications include antibacterial applications. It will be appreciated that there are many applications for such methods and materials including in infection control. Of particular interest within the present invention are infection control applications in human and veterinary medicine such as in surface cleaning. Also of particular interest are infection control of materials entering the body, for example, implants etc.

The present invention also relates to an article of commerce which comprises a composition having an amyloid precursor peptide or protein and a conversion agent for converting the protein into an amyloid fibril or amyloid-like fibril confirmation. In such an article of commerce the protein may be solubilised or that the conversion agent may be a catalyst for example metal ions or amyloid seed or denaturant for example urea, SDS, guanidine hydrochloride. It is also possible that the conversion agent is an enzyme.

Further embodiments disclose an article of commerce which comprises a composition having a suitable precursor material such as peptide or protein, wherein the protein is converted into an amyloid fibril or amyloid-like fibril conformation by one or more of the following: (1) upon contact with the atmosphere; (2) Upon contact with water; (3) Upon exposure to radiation such as UV radiation; (4) Upon contact with an amyloid or amyloid-like form of a protein or peptide; (5) Upon heating; (6) Upon a suitable change in pH; (7) Upon a combination of two or more of the preceding conditions (1)-(6).

A further embodiment relates to an article of commerce comprising a material that has been mechanically strengthened by synthetic amyloid-like peptide or protein or synthetic amyloid-like fibrils.

The invention also discloses an article of commerce comprising two substrates bonded together by any of the compositions as mentioned above and further describes an article of commerce comprising a material coated with an enteric coating which comprises synthetic amyloid-like peptide or protein for example fibrils.

The present inventors have shown that amyloid-like fibrils can be formed from a fruit or vegetable protein. These amyloid fibrils can further form a fibrous material. The invention also relates to a method of enhancing the adhesive or mechanical strength properties of a substance for example by adding to the substance, or generating in situ, a synthetic or isolated amyloid-like peptide or protein fibril.

The invention also provides a method of adhering cells to a substrate comprising the step of causing the cells to secrete material or present such material on their cell-surface so as to form amyloid protein fibrils or amyloid-like proteins or peptides. While the amyloid or amyloid-like fibril can be used as an adhesive or as an additive for an adhesive, a method of inhibiting adherence of marine and/or terrestrial life forms to a structure such as a ship's hull is also disclosed. The method comprises treating the structure with an inhibiting agent for inhibiting the formation of amyloid, for example wherein the agent is selected from aromatic residues such as phenylalanine, phenylsulfonphthalein (phenol red), catechins and curcumin and combinations thereof.

BRIEF DESCRIPTION OF THE DRAWINGS

FIG. 7. TEM images showing amyloid-like fibrils grown in 50 mM Tris HCl, pH 7.4 for 17 days at 37° C.

FIG. 8. AFM image of amyloid fibril grown in 50 mM Tris HCl, pH 7.4 for 10 days at 37° C. The height trace represents the section indicated by the red line in the image (see also Table 1 below).

DETAILED DESCRIPTION AND EXPERIMENTAL WORK

Figure 1:
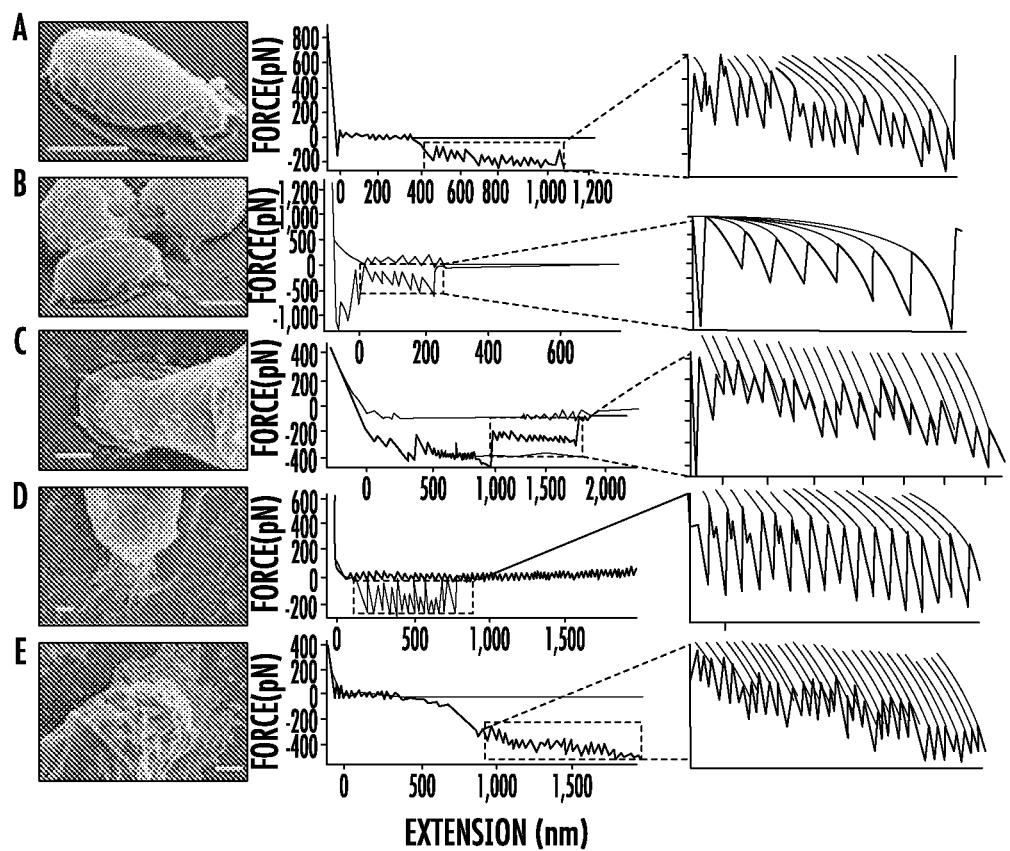
FIG. 1. Scanning electron micrographs showing attachment structures of terrestrial algae attached to glass coverslips. Scale bars=2 µm. Adhesive pads are shown beneath cells of a, *C. angustoellipsoidea* and b, *C. trebouxiodes*. AFM force measurements were made on the cell-pad interface. Adhesive holdfasts are observed at the base of differentiated blades of c, *P. calophylla* and d, *P. linearis*, and e, at the base of *K. flaccidum* filaments. Force measurements were made directly on the exposed region of the holdfasts. Beside each species are representative AFM force-extension curves showing sawtooth structures. Both the approach (red) and retraction (blue) force traces are shown. Sawtooth structures such as these occurred frequently in localized regions. Force curves were obtained in culture medium using a commercial AFM (MFP-3D, Asylum Research, CA) mounted on top of an inverted optical microscope, taken at a rate of 0.1 to 0.5 Hz using $Si_3N_4$ cantilevers with calibrated spring constants between 0.2 and 0.5 $Nm^{-1}$. Expansions of the sawtooth region of each force-extension curve are also shown fitted to the worm-like chain model (dotted lines).

As examples of the present invention, the nanoscale adhesive properties of five terrestrial algal species are demonstrated, selected because of their great ecological success in coping with environmental stress and their observed strong attachment to surfaces. *Prasiola* is a multicellular green macroalgal genus. *P. calophylla* forms abundant patches of ribbon-like blades in the damp urban habitats of western Ireland and *P. linearis* occurs attached to grasses of coastal lagoons. *Klebsormidium flaccidum* is an unbranched, filamentous green alga common in Mediterranean areas where it forms patches at the base of old walls. In contrast, *Chlorella angustoellipsoidea* and *C. trebouxiodes* are unicellular green microalgae that form extensive films on exposed roof tiles and building facades. Strong attachment includes a reversible attachment. For example the marine parasite Entobdela Soleae successfully attaches to its host fish (usually sole) but can detach and re-attach itself.

Scanning electron microscopy of both *Chlorella* species reveals an EPS layer covering the cell surface, and a differentiated region of EPS secreted beneath the cell forming a discrete adhesive pad for strong adhesion (FIGS. 1a, b). Similarly, *Prasiola* and *K. flaccidum* spores have a mucilaginous coating, but distinct adhesive holdfast structures are located at the base of differentiated plants (FIGS. 1c-e). It is apparent that these structures function specifically for permanent adhesion. It will be appreciated that certain life forms for example *Entobdela Soleae* can attach and detach many times.

While the chemical composition of algal EPS and morphology of algal attachment structures have been the subject of previous studies[2], the present invention provides the first direct evidence for a sophisticated ultrastructure within these natural adhesives. AFM has already proved to be a key tool for measuring the mechanical properties of single molecules such as modular proteins[5], DNA[6,7] and polysaccharides[8,9]. Frequently, specific molecular types were associated with a particular nano-mechanical signature[10]. In particular, the force-extension profile of modular proteins such as titin exhibit a highly ordered sawtooth pattern of regularly spaced adhesion peaks corresponding to the sequential unfolding of the individual polypeptide domains under a tensile force[11,12]. When fitted to the worm-like chain model these modular proteins exhibited characteristic persistence lengths corresponding to an individual amino acid subunit[5]. It has been suggested that the successive release of 'sacrificial bonds' within modular proteins may be the molecular mechanistic origin of the toughness of natural fibres and adhesives[13]. Although all modular proteins explored with atomic force microscopy (AFM) have shown a similar mechanical sawtooth profile[5], it is important to realise that such a profile is not unique to modular proteins as has been suggested[14]. Indeed, any repetitive ultrastructure could in principle provide such a signature.

AFM was used to investigate the mechanical properties of the adhesive substances of algal cells and a marine parasite under ambient conditions. Surprisingly, the resulting force-extension curves showed a characteristic sawtooth pattern of regularly spaced peaks, which is associated with materials exhibiting high mechanical strength due to the high energy required to break successive sets of 'sacrificial bonds'[13]. Even more surprisingly, the pattern was found to be (potentially) reversible when (in certain cases) the material did not detach from the AFM tip between successive curves, indicating a strong ability of the material to refold or re-assemble. Worm-like chain fitting[15] to the elastic response of the adhesion peaks revealed a mean persistence length of 0.44±0.08 nm for *C. angustoellipsoidea* (FIG. 1a), 0.17±0.07 nm for *C. trebouxiodes* (FIG. 1b), 0.50±0.15 nm for *P. calophylla* (FIG. 1c), 0.34±0.18 nm for *P. linearis* (FIG. 1d), and 0.11±0.02 nm for *K. flaccidum* (FIG. 1e). In the case of proteinaceous structures, the persistence length should relate to the dimensions of the constituent amino acid building blocks as observed previously[11]. The majority of the persistence length values are consistent with those given for other proteins such as titin (0.4 nm)[11,12], and tenascin (0.42 nm)[16], but the smaller persistence lengths observed for *C. trebouxiodes* and *K. flaccidum* indicates that the material, while probably proteinaceous, is not always single stranded.

While it may be appealing to attribute the observed sawtooth mechanical signatures, persistence length and reversibility to modular proteins[17], the present invention surprisingly considers alternative structures. Once the observed persistence length becomes 'unphysical', in other words significantly smaller than that for an amino acid, the restraints on mechanical models of multiple modular proteins acting in parallel to give the observed mechanical signatures become so complex as to be implausible. For example, a parallel arrangement of molecules could produce a regularly spaced sawtooth mechanical signature with small persistence length, however, this will only give a regularly spaced domain length if each modular protein contains exactly the same number of modules between tip and sample, which is highly unlikely even if both were completely smooth parallel surfaces. When viewed in this light, it is difficult to imagine a plausible arrangement of an equal number of modules in each strand without invoking some regularly spaced linking side chains between them such as some form of glycoprotein with modular backbone. However, in this arrangement it is arguable as to whether the multiple ends of the modular protein strands are likely to form the only connection to the tip and substrate to the total exclusion of the side chains. For example, if the tip comes into contact with the side rather than the end of the multimolecular fiber the applied force becomes totally mediated via the side chains and the uniform extension of the modular units will be completely lost as will the repetitive sawtooth structure. Full modelling of far less complex mechanical arrangements of single molecule based mesostructures have shown no regular persistence or domain length[18].

In addition, modular proteins have unique and specific amino-acid sequences that should be detectable in sequencing. Despite some immunological evidence for vitronectin-like glycoproteins in the adhesive matrix of the brown alga *Fucus*[19] and the green alga *Caulerpa*[20], the increasing amount of sequencing data currently being compiled worldwide has yet to provide compelling evidence for the ubiquitous presence of modular proteins in natural adhesives. The present invention provides an alternative mechanism based on a generic ultrastructure that does not depend on a specific amino-acid sequence. Nature has a generic structure of this type that surprisingly have been found to readily self-assemble from most polypeptides under appropriate conditions (usually slightly denaturing), known as amyloid fibrils[21]. These fibrils consist of proteins, or protein fragments in the case of model fibrils synthesized in vitro, that self-assemble in beta-sheet-rich structures. Certain proteins are considered to be more amyloidogenic than others, but such proteins have already been found to be ubiquitous in nature[22] so their presence in all natural adhesives is entirely plausible.

Figure 2:
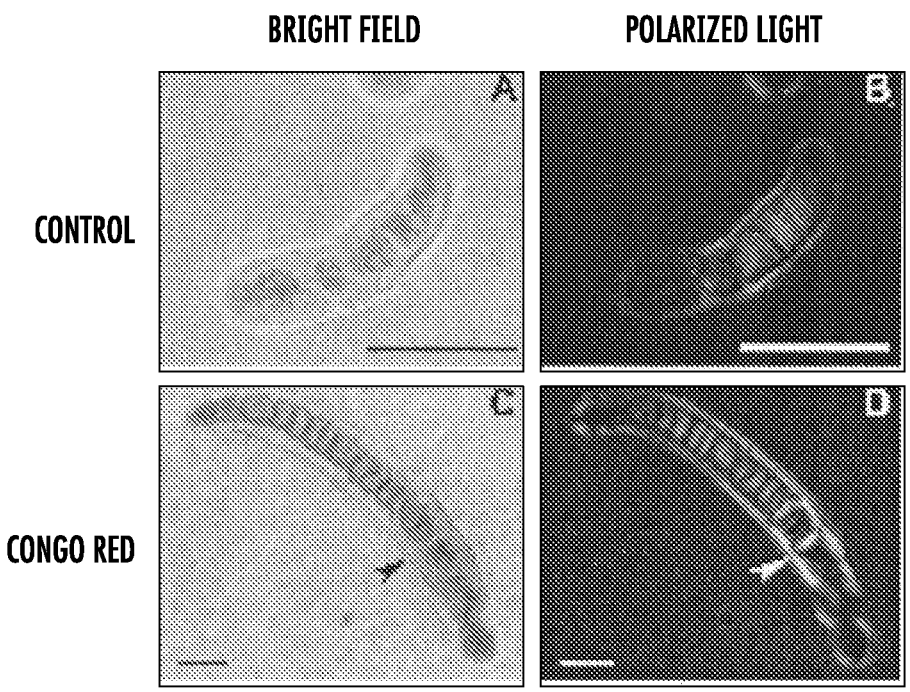
FIG. 2. Young sporelings of *P. linearis* growing attached to glass coverslips. Unstained control plant is shown with a, bright field and b, cross-polarized light showing a faint autofluorescence. c, d, Plant treated directly with Congo red dye. a, Bright-field microscopy showing binding of the dye in the adhesive region of the algal frond (arrow), and b, the same region showing green-gold birefringence under cross-polarized light (arrow) characteristic of amyloid deposits. As birefringence is dependent on the thickness of the sample, the most pronounced positive result was seen in our larger, multicellular material such as this species. Scale bars=25 µm.

To verify the presence of amyloid structures in our algal adhesive we used the amyloid selective Congo red dye that preferentially binds to amyloid over other types of protein aggregates[23]. The characteristic green-gold birefringence observed with cross-polarized light after staining with Congo red dye confirms that indeed amyloid structures are present and can be readily detected in our multicellular material (FIG. 2).

Model amyloid fibrils formed from transthyretin ($TTR_{105-115}$) peptide fragments deposited onto a mica surface were studied to determine whether amyloid fibrils can in principle produce sawtooth mechanical signatures. In recent years significant efforts have been made to determine and understand the complex molecular structure of amyloid fibrils[24] by investigating fibrils formed in vitro from short peptide segments[25]. Model fibrils typically consist of short peptide sections folded into beta-strands and self assembled into beta-sheets that stack to form fibrils. Such fibrils are studied extensively in an attempt to understand the formation of amyloid fibrils in neurodegenerative diseases such as Alzheimer's and Parkinson's diseases although there still remain a number of unknowns regarding the actual self-assembly process and the internal structure of the fibrils.

By first imaging the fibrils (FIG. 3a) it was possible to pull at specific points along the length of the fibrils. Many varied mechanical responses were observed with random force peaks and plateaus predominating, as highlighted previously by Kellermayer et al.[26] Occasionally a sawtooth signature was observed as shown in FIG. 3b. While not wishing to be bound by theory, it is believed that the sawtooth relates to the sequential stretching of the beta-strands so as to be end to end rather than in their parallel arrangement within the fibril. The magnitude of the force at the point the bonds rupture is approximately 20 pN and relates to both the number and type of bonds between the beta-strands. Interestingly, the sawtooth shown here (FIG. 3c) is remarkably similar to that observed by Lee et al.[27] for the sequential unfolding of individual ankyrin repeats consisting of antiparallel alpha-helices (FIG. 2 of Lee et al.[27]). This is further evidence that regular mechanical responses cannot be regarded as 'fingerprints' unique to a particular molecular type or conformation. Instead they should be regarded as an indication of repetitive structure requiring further investigation by alternative non-mechanical methods.

Figure 3:
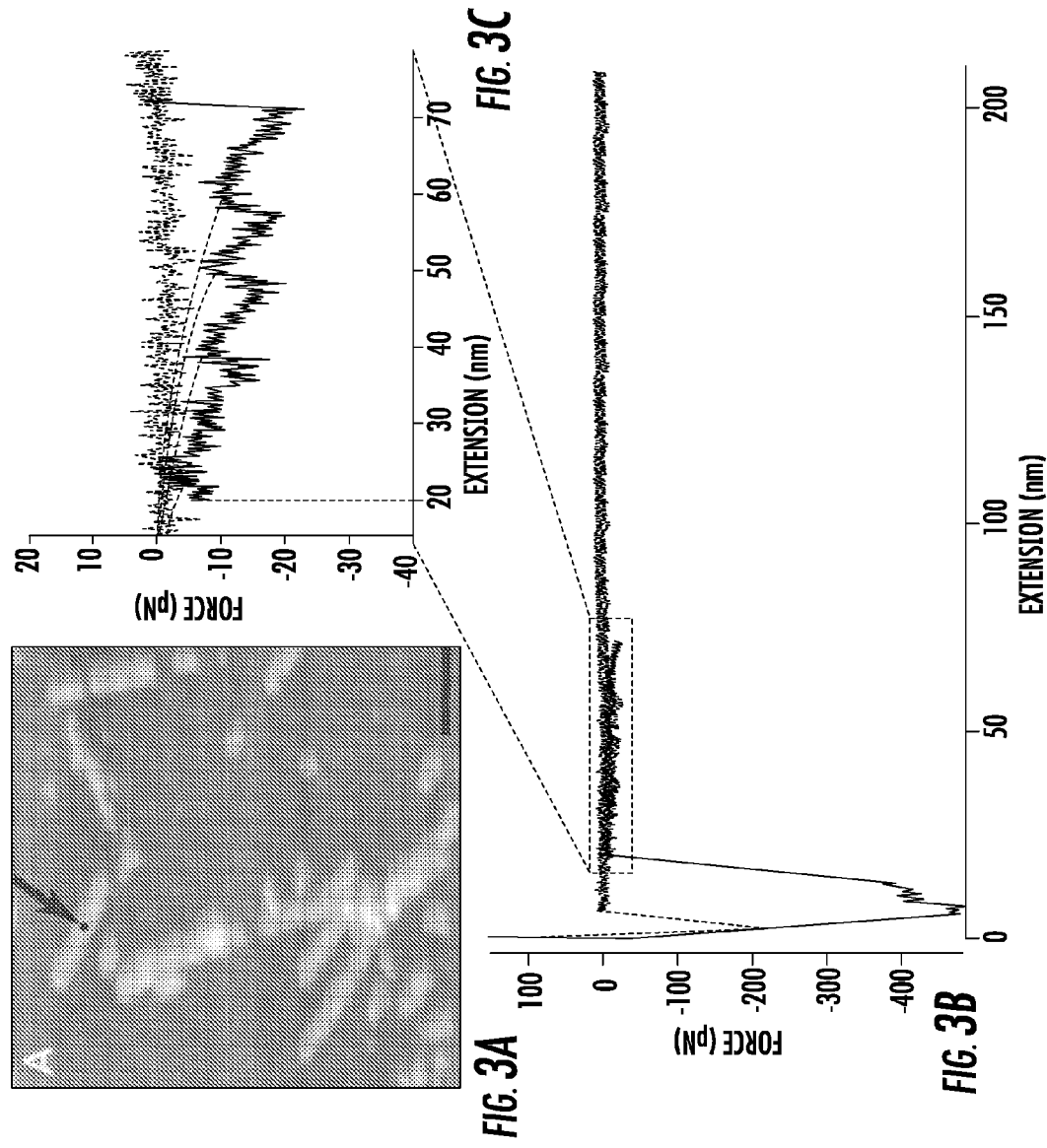
FIG. 3. a, $TTR_{105-115}$ amyloid fibrils deposited onto mica and imaged in intermittent-contact mode using a home-built AFM. Scale bar=400 nm. b, Force-extension curve obtained in static mode for the fibril marked with the arrow in a. c, Expansion of the sawtooth region indicated in b, fit to the worm-like chain model (dotted lines). Data in C, has been averaged over five data points. Measurements were made in PBS buffer using a Si cantilever with a spring constant of 0.065 $Nm^{-1}$.
Figure 4:
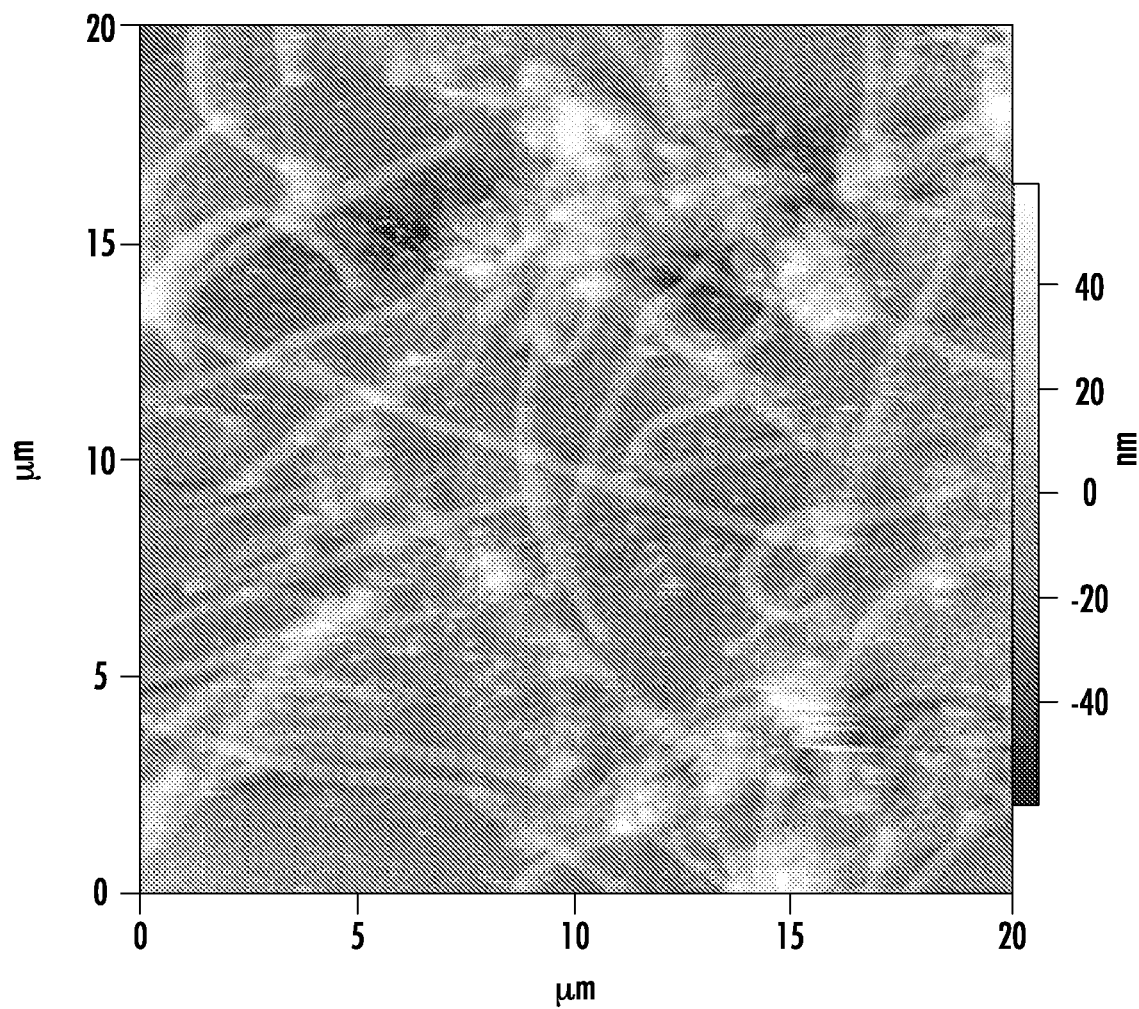
FIG. 4. AFM image of the temporary adhesive secreted by the marine parasite *Entobdella Soleae*. The primary component of the adhesive consists of amyloid ribbons.
Figure 5:
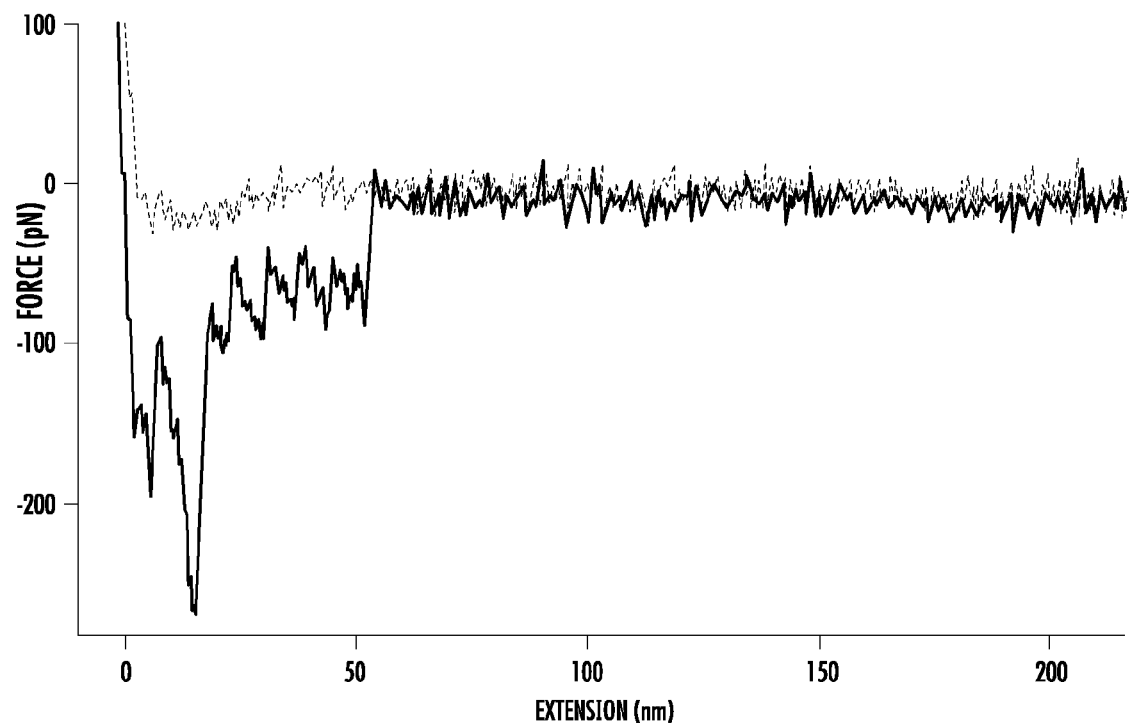
FIG. 5. Representative AFM force-extension curves, taken on the temporary adhesive of *Entobdella Soleae*, showing sawtooth structures. Force curve was taken by pulling directly on the sub-structure of the amyloid ribbons. Both the approach (upper trace in Figure) and retraction (lower trace in Figure) force traces are shown.

A similar pattern to that shown in FIG. 3 is shown in FIG. 5. FIG. 5 shows an AFM image of the temporary adhesive secreted by the marine parasite *Entobdella Soleae*. The primary component of the adhesive consists of amyloid ribbons which are clearly identifiable from FIG. 4. In a manner analogous to that described for FIG. 3 the representative AFM force-extension curves (illustrated in FIG. 5), were taken on the temporary adhesive of *Entobdella Soleae*, and are indicate sawtooth structures. The force curve was taken by pulling directly on the sub-structure of the amyloid ribbons. Both the approach (upper trace in Figure) and retraction (lower trace in Figure) force traces are shown.

Figure 6:
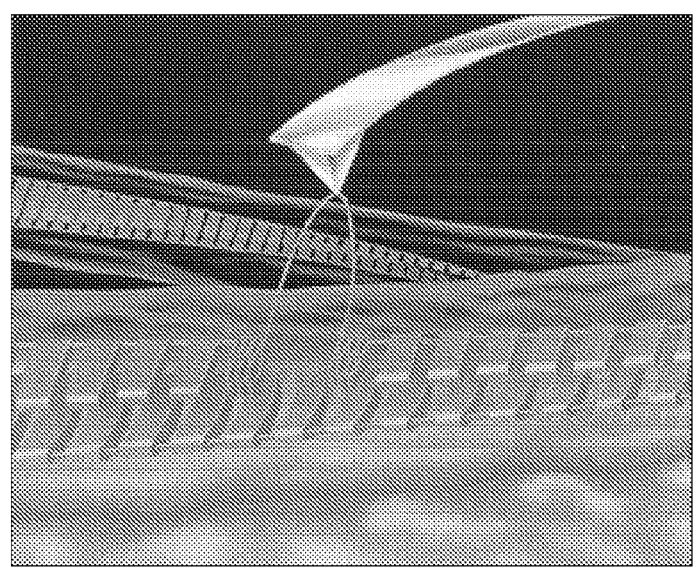
FIG. 6. Schematic model of the mechanical manipulation of an amyloid fibril by AFM. The schematic of the amyloid fibril is not intended to suggest a specific molecular structure within the fibrin. Molecular level structural data on amyloid fibrils formed from proteins, as opposed to peptide fragments, remains scarce. The schematic shows interacting molecular building blocks of multiple beta-strands running perpendicular to the direction of the fibre (beta-strand detail is shown below the tip).

Although qualitative similarities are observed between the mechanical responses of amyloids formed from peptide fragments and those formed from proteins in our natural materials, exact quantitative agreements are not observed. Based on the present invention, it is reasonable to expect there to be a significant dependence of the measured forces and the distance between the peaks on the number of amino acids in the constituent proteins or polypeptide fragments. Each protein molecule or polypeptide fragment will form a beta-strand or strands depending on their length. These then stack with other beta-strand molecules or fragments to form a 'track' or beta-sheet as shown schematically in FIG. 6. The peak force should increase if there are a greater number of amino-acids in the constituent molecules or fragments. This would be in agreement with the results of Kellermayer and co-workers[26], who sometimes observe non-linear elastic behaviour when pulling on fibrils formed from A beta$_{14}$ peptide fragments with peak forces exceeding 100 pN and a persistence length of 0.38 nm. An unphysically small persistence length would be observed if more than one set of (intermolecular) beta-sheets were attached to the tip.

Thus the mechanical manipulation of beta-sheets (or multiple layers thereof) within the repetitive amyloid ultrastructure provides an alternative simple mechanism that allows for the observed amino-acid persistence length correspondence as well as the short persistence lengths in some of our adhesives. Functional amyloid (amyloidin)[28] may provide a generic mechanism for mechanical strength in natural adhesives and other natural materials.

In favourable embodiments of the invention, proteins with at least about 50, and preferably at least about 200 amino acids are used. Generally within the present invention peptides will be considered to have less than 50 amino acids. Surprisingly, it was found that typical peptide fragments with an amino acid length of from about 4 to about 20 may not be sufficiently long to acquire a desired mechanical strength. While not wishing to be bound by theory the reason for this may be that longer protein structures have greater amounts of folding and bonding and therefore may provide greater mechanical strength as these can form larger beta-strand structures. Thus, while the present invention indicates that natural amyloid may be the biological equivalent of carbon nanotubes in terms of providing mechanical strength to composite materials, their synthesized equivalents from peptide fragments are unlikely to exhibit the same beneficial mechanical properties, and it is believed that the compositions, cells and methods of the invention functions with increased efficacy with peptides or proteins of at least about 20 amino acids, preferably over about 30 amino acids, and more preferably over about 40 amino acids. Heretofore amyloid has been utilised for research into neuro-degenerative diseases and is typically constructed of short (typical length is 10 amino acids) protein fragments (peptides). Desirably within all aspects of the present invention proteins with 180 to 500 amino acids are employed, for example 200 to 480, such as 210 to 460, desirably 220 to 440. For example a common potato protein (patatin) has about 380 amino acids of which about less than 10% are glutamine. Such parameters apply also to the Ovalbumin and related proteins described by Pearse et al in the literature reference described above.

Until now, finding any connection between the generic mechanical strength of natural adhesives has proved elusive, because the amino acid composition of those adhesives that have been sequenced have frequently been found to be unique to a particular species. Although a number of research groups investigating natural adhesives of great diversity have remarked upon the observation of proteinaceous fibers made of beta-pleated sheets[29,30,31,32], the fact that the amyloid ultrastructure does not have a specific amino acid motif may be the very reason why it has remained so elusive. Experiments indicate that amyloid formation from a protein with a stable monomeric structure does not necessitate that the entire protein participates in the amyloid core structure[33]. Thus additional protein domains that may contain species-specific adhesive residues can retain their native function external to the fibril core structure. The present invention indicates that while the mechanism for mechanical strength in natural adhesives may be attributed to generic amyloid structures (i.e., mechanical amyloidin), evidence would suggest that the mechanism for adhesion itself remains species specific.

There is recent evidence that functional amyloidogenesis can exhibit, together with some similarities, a number of striking differences when compared to pathogenic amyloid formation.[28]

EXAMPLES

Protein Extraction

Protein recovery from potato juice (PJ) is performed industrially through pH changes and heat coagulation, but is considered a by-product of starch manufacturing with low value[34]. The present invention provides a simple method of extracting the juice from locally grown potatoes, and preparing amyloid-like structures from this solution under laboratory conditions. In order to form bio-materials such as bio-adhesives or bio-films of commercial value it is desirable to have a protein source that is inexpensive and accessible. Potato protein fits this criteria. In particular, potato peel waste from potato processing plants is readily available and at present has virtually no value.

Preparation of Potato Juice (PJ)

Irish potatoes were purchased from a local supermarket and the juice prepared following the method of van Koningsveld et al.[34,35]. Approximately 250 gm of potatoes were washed with water, cut into large chunks, and dipped into 20 mg/ML sodium bisulfite. The unpeeled potato pieces were processed into a domestic juicer (Breville) and the juice allowed to settle for 30 mins. The liquid was decanted from the settled sediment and centrifuged at 14,000 g at room temperature for 15 mins. The resultant supernatant (PJ) was filtered (Millex-GS 0.22 μm) and stored at −20° C. until used. The PJ is a heterogeneous protein source of 3 protein classes and had a pH of 5.9.

Preparation of Treatment Solutions and Incubation Conditions.

In 1.5 m eppendorf tubes, 0.5 mL of PJ was added to 0.5 mL of a range of buffers and solutions with and without 2 M urea (Sigma) as a denaturant. One sample from each buffer set was 'seeded' to induce amyloid formation by the addition of 10 μL amyloid solution. This was grown from 1 mM amylin (H-7905, Bachem) in TRIS-HCl, pH 7.4 at 37° C. for 5 days. These various treatments are given in Table 1.

Samples were incubated at 25° C. for 12 hours in order to assess whether amyloid-like structures could form rapidly at room temperature, and others were incubated at 37° C. for 10 days. Aliquots of 200 μL were removed at each of the 2 treatment time intervals and frozen at −20° C. until analysed.

Thioflavin T (ThT) Fluorescence Assay.

Thioflavin T (Sigma™) was used to detect beta-sheet rich amyloid-like structures and aggregates using the method of LeVine[36]. Fluorescence emission intensity was recorded using an excitation wavelength of 465 nm and emission wavelength of 514 nm using a Tecan plate reader. ThT stock dye solutions were prepared at 10 μM in each of the treatment buffers. In 96-well plates 200 μL of ThT dye in the appropriate buffer was added to 50 μL of each corresponding sample and allowed to bind for 5 minutes before readings were made. Controls of buffer alone, buffer with sample, and buffer with ThT were also measured.

Atomic Force Microscope (AFM) Imaging.

50 μL of sample was deposited directly onto coverslips that had been cleaned by sonicating in acetone, washing in Milli-Q water, and then drying with a $N_2$ gas stream. The sample was left to incubate for 2 hours at room temperature. Unbound material was gently rinsed from the surface with Milli-Q water, dried with a $N_2$ gas stream, and imaged directly in air using a MFP-3D AFM (Asylum Research). Images were made in intermittent-contact mode using silicon cantilevers (NCHR, Nanosensors) with a spring constant of 40 $Nm^{-1}$, and at typical scanning rate of 1 Hz.

Transmission Electron Microscopy (TEM).

Samples at 17 days incubation at 37° C. were negatively stained for TEM observation. 10 μL of sample was deposited directly onto formvar-coated 300 mesh copper grids and left to adhere to the coating for 2 hours at room temperature. Excess material was removed with filter paper and grids were stained for 3 min with filtered 0.05% aqueous uranyl acetate. Grids were washed by gently dipping in distilled water and allowed to air dry. Specimens were viewed using a Jeol JEM-2000 FX II TEM at an accelerating voltage of 100 kV.

TABLE 1

Incubation conditions up to 10 days of PFJ. Positive (+) or negative (−) results for amyloid-like structures detected using ThT fluorescence are shown. All controls were negative. TEM observations showing beta-sheet aggregate structures only (A), or amyloid fibrils (F) (FIG. 1). (−) samples not yet observed.

| Incubation solution | 12 hrs at 25° C. | 10 days 37° C. | TEM observation |
|---|---|---|---|
| 1. SDS | ++ | +++* | A |
| SDS + 2 M Urea | ++ | ++ | A |
| SDS + Seeding | ++ | +++ | F |
| 2. Phosphate buffer | + | + | − |
| Phosphate buffer + 2 M Urea | + | ++ | − |
| Phosphate buffer + Seeding | − | − | − |
| 3. Water | + | + | − |
| Water + 2 M Urea | − | − | − |
| Water + Seeding | − | + | − |
| 4. PBS | − | − | F |
| PBS + 2 M Urea | + | + | F |
| PBS + Seeding | + | + | F |
| 5. TRIS | + | + | F |
| TRIS + 2 M Urea | + | ++** | F |
| TRIS + Seeding | + | + | F |

1. 0.5% SDS in 0.05M phosphate buffer, pH 7.4
2. Phosphate buffer, 0.05 M, pH 7.4
3. Milli-Q (Millipore) Ultrapure water
4. Phosphate buffered saline (Sigma), pH 7.4
5. 50 mM TRIS HCl, pH 7.4
*AFM imaging indicating the presence of aggregates only
**AFM imaging indicating the presence of fibrils (see FIG. 8)

Example of Adhesive Composition

To test whether the addition of amyloid-like protein fibrils to a filler could strengthen adhesion between surfaces, 2 glass slides were attached with 90 μL of glycerol gelatin (Sigma) together with 10 μL of amyloid solution. The amyloid solution was the same as that shown in FIG. 7, where amyloid-like fibrils were grown from PJ in 50 mM Tris HCl, pH 7.4 for 17 days at 37° C. Gycerol gelatin was liquefied before use by warming to 50° C., and the slides were incubated at 37° C. overnight. When the slides cooled to room temperature, the slides could not be separated without breaking the glass, demonstrating a strong bond.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

1. Westermark, P. et al. Amyloid fibril protein nomenclature. *Amyloid-Carnforth*-9, 197-200 (2002).
2. Fletcher, R. L. & Callow, M. E. Settlement, attachment and establishment of marine algal spores. *Br. PhycoL J.* 27, 303-329 (1992).
3. Loske, C. et al. Transition metal-mediated glycoxidation accelerates cross-linking of β-amyloid peptide. *Eur. J. Biochem.* 267, 4171-4178 (2000).

4. Sever, M. J., Weisser, J. T., Monahan, J., Srinivasan, S. & Wilker, J. J. Metal-mediated cross-linking in the next generation of a marine-mussel adhesive. *Angew. Chem. Int. Ed. Engl.* 43, 448-450 (2003).
5. Best, R. B. & Clark, J. What can atomic force microscopy tell us about protein folding? *Chem. Commun.* 18, 183-192 (2002).
6. Lee, G. U., Chrisey, L. A. & Colton, R. J. Direct measurement of the interaction forces between complementary strands of DNA with atomic force microscopy. *Science* 266, 771-773 (1994).
7. Rief, M., Clausen-Schaumann H. & Gaub H. E. Sequence-dependent mechanics of single DNA molecules. *Nature Struct. Biol.* 6, 346-349 (1999).
8. Marsalek, P. E., Oberhauser, A. F., Pang, Y-P. & Fernandez, J. M. Polysaccharide elasticity governed by chair-boat transitions of the glucopyranose ring. *Nature* 396, 661-664 (1998).
9. Rief, M., Oesterhelt, F., Heymann, B. & Gaub, H. E. Single force spectroscopy on polysaccharides by atomic force microscopy. *Science* 275, 1295-1297 (1997).
10. Fisher, T. E., Marszalek, P. E. & Fernandez, J. M. Stretching single molecules into novel conformations using the atomic force microscope. *Nature Struct. Biol.* 7, 719 724 (2000).
11. Rief, M., Gautel, M., Oesterhelt, F., Fernandez, J. M. & Gaub, H. E. Reversible unfolding of individual titin immunoglobulin domains by AFM. *Science* 276, 1109 1112 (1997).
12. Tskhovrebova, L., Trinick, J., Sleep, J. A. & Simmons, R. M. Elasticity and unfolding of single molecules of the giant muscle protein titin. *Nature* 387, 308-312 (1997).
13. Smith, B. L. et al. Molecular mechanistic origin of the toughness of natural adhesives, fibres and composites. *Nature* 399, 761-763 (1999).
14. Fernandez, J. M. Fingerprinting Single Molecules In Vivo. *Biophys. J.* 89: 3676-3677 (2005).
15. Bustamante, C., Marko, J. F., Siggia, E. D. & Smith, S. Entropic elasticity of λ-phage DNA. *Science* 265, 1599-600 (1994).
16. Oberhauser, A. F., Marszalek, P. E., Erickson, H. P. & Fernandez, J. M. The molecular elasticity of the extracellular matrix protein tenascin. *Nature* 393, 181-185 (1998).
17. Dugdale, T. M., Dagastine, R., Chiovitti, A., Mulvaney, P. & Wetherbee, R. Single adhesive nanofibres from a live diatom have the signature fingerprint of modular proteins. *Biophys. J.* 89, 4252-4260 (2005).
18. Fantner, G. E. et al. Sacrificial bonds and hidden length: Unraveling molecular mesostructures in tough materials. *Biophys. J.* doi:10.1529/biophysj.105.069344 (2005).
19. Wagner, V. T., Brian, L. & Quatrano, R. S. Role of vitronectin-like molecule in embryo adhesion of the brown alga *Fucus*. *Proc. Natl Acad. Sci. USA* 89, 3644-3648 (1992).
20. Levi, B. & Friedlander, M. Identification of two putative adhesive polypeptides in Caulerpa prolifera rhizoids using an adhesion model system. *J. Appl. Phycol.* 16, 1-9 (2004).
21. Dobson, C. M. Protein Folding and Misfolding. *Nature* 426, 884-890 (2003).
22. Bateman, A. et al. The Pfam protein families database. *Nucleic Acids Res*. Database issue 32, D138-D141 (2004).
23. Vowles, G. H. & Francis, R. J. in Theory and Practice of Histological Techniques, 5$^{th}$ ed. (eds Bancroft, J. D. & Gamble M.) 303-324 (Churchill Livingstone, Harcourt, London, 2002).
24. Tycko, R. Progress towards a molecular-level structural understanding of amyloid fibrils. *Curr. Opin. Struct. Biol.* 14, 96-103 (2004).
25. Gazit, E. Mechanisms of amyloid fibril self-assembly and inhibition: Model short peptides as a key research tool. *FEBS J.* 272, 5971-5978 (2005).
26. Kellermayer, M. S. Z. et al. Reversible mechanical unzipping of amloid β-fibrils. *J. Biol Chem.* 280, 8464-8470 (2005).
27. Lee, G. et al. Nanospring behaviour of ankyrin repeats. *Nature* dio: 10.1038/nature.04437 (2006).
28. Fowler, D. M. et al. Functional Amyloid formation within mammalian tissue. *PloS Biol.* 4, doi: 10.1371/joumal.pbio.0040006 (2006).
29. Hamwood, T. E., Cribb, B. W., Halliday, J. A., Kearn, G. C. & Whittington, I. D. Preliminary characterisation and extraction of anterior adhesive secretion in monogenean (platyhelminth) parasites. *Folia Parasitol.* 49, 39-49 (2002).
30. Waite, J. H., Lichtenegger, H. C., Stucky, G. D. & Hansma, P. Exploring Molecular and mechanical gradients in structural bioscaffolds. *Biochemistry.* 43, 7653-7662 (2004).
31. Whittington, I. D. & Cribb, B. W. Adhesive secretions in the Platyhelminthes. *Adv. Parasitol.* 48, 101-224 (2001).
32. Kamino, K. et al. Barnacle cement proteins. *J. Biol. Chem.* 275, 27360-27365 (2000).
33. Baxa, U., Speransky, V., Stevens, A. C. & Wickner, R. B. Mechanism of inactivation on prion conversion of the Saccharomyces cerevisiae Ure2 protein. *Proc. Natl. Acad. Sci. USA* 99, 5253-5260 (2002).
34. van Koningsveld, G. A., Gruppen, H., De Jongh, H. H. J., Wijngaards, G., Van Boekel, M. A. J. S., Walstra, P. & Voragen, A. G. J. The solubility of potato proteins from industrial fruit juice as influenced by pH and various additives. J. Sci. Food Agric. 82, 134-142 (2001).
35. van Koningsveld, G. A., Gruppen, H., De Jongh, H. H. J., Wijngaards, G., Van Boekel, M. A. J. S., Walstra, P. & Voragen, A. G. J. (2002). Effects of ethanol on structure and solubility of potato proteins and the effects of its presence during the preparation of a protein isolate. *J. Agric. Food Chem.* 50, 2947-2956 (2002).
36. LeVine III, H. (1999) Quantification of β-sheet amyloid structures with thioflavin T. Methods Enzymol. 309: 274-284.

The invention claimed is:
1. A synthetic adhesive composition comprising:
an amyloid-like component having a cross beta sheet quaternary structure, the amyloid-like component comprising at least one peptide or protein having an adhesion group;
wherein the peptide or protein is selected from the group consisting of fruit protein, fruit peptide, vegetable peptide, vegetable protein, banana peptide, banana protein, potato peptide and potato protein.
2. A composition according to claim 1 wherein the amyloid-like component is formed from an amyloid precursor peptide or protein.
3. A composition according to claim 1 wherein the amyloid-like component is in the form of fibrils.
4. A sealant composition comprising:
an amyloid-like component having a cross beta sheet quaternary structure, the amyloid-like component comprising at least one peptide or protein; and a curable component;
and in which said amyloid-like component imparts mechanical strength to the cure product of the curable component.

5. A synthetic adhesive composition comprising a curable component; and
an amyloid-like component having a cross beta sheet quaternary structure, the amyloid-like component comprising at least one peptide or protein having an adhesion group.

6. A composition according to claim 5 further comprising a cure component for curing the curable component.

7. A sealant composition according to claim 4 further comprising a cure component for curing the curable component.

\* \* \* \* \*

UNITED STATES PATENT AND TRADEMARK OFFICE
CERTIFICATE OF CORRECTION

| | | |
|---|---|---|
| PATENT NO. | : 7,851,434 B2 | Page 1 of 1 |
| APPLICATION NO. | : 11/685443 | |
| DATED | : December 14, 2010 | |
| INVENTOR(S) | : Suzanne P. Jarvis and Anika S. Mostaert | |

It is certified that error appears in the above-identified patent and that said Letters Patent is hereby corrected as shown below:

In the Specification:

In the Summary of the Invention, Column 2, Line 49 delete "WO 2005/03313"

and insert -- WO 2005/033131 --

Signed and Sealed this
Twenty-fifth Day of January, 2011

David J. Kappos
*Director of the United States Patent and Trademark Office*